United States Patent [19]

New et al.

[11] Patent Number: 4,619,930

[45] Date of Patent: Oct. 28, 1986

[54] ANTIPSYCHOTIC CYCLIC IMIDE DERIVATIVES OF 2-(4-BUTYLPIPERAZIN-1-YL)PYRIDINES, COMPOSITIONS AND USE

[75] Inventors: James S. New; Walter G. Lobeck, Jr., both of Evansville; Joseph P. Yevich, Newburgh, all of Ind.

[73] Assignee: Bristol-Myers Company, New York, N.Y.

[21] Appl. No.: 691,952

[22] Filed: Jan. 16, 1985

[51] Int. Cl.$^4$ .................. A61K 31/495; C07D 417/14; C07D 513/10

[52] U.S. Cl. .................................. 514/252; 514/253; 544/230; 544/364; 544/121; 544/58.2

[58] Field of Search ................. 544/230, 364; 514/252, 514/253

[56] References Cited

U.S. PATENT DOCUMENTS

| | | | |
|---|---|---|---|
| 3,717,634 | 2/1973 | Wu et al. | 544/230 |
| 3,907,801 | 9/1975 | Wu et al. | 544/230 |
| 4,305,944 | 12/1981 | Temple, Jr. et al. | 544/230 |
| 4,361,565 | 11/1982 | Temple, Jr. et al. | 544/364 |
| 4,367,335 | 1/1983 | Temple, Jr. et al. | 544/295 |
| 4,456,756 | 6/1984 | Temple, Jr. et al. | 544/364 |

OTHER PUBLICATIONS

Wu et al., J. Med. Chem., 15, 447–479 (1972).

*Primary Examiner*—Robert W. Ramsuer
*Attorney, Agent, or Firm*—Richard P. Ryan

[57] ABSTRACT

Disubstituted N,N-piperazinyl derivatives are disclosed wherein one substituent is a substituted pyridin-2-yl ring and the second substituent is a butylene chain attached to cyclic imide heterocycles such as azaspiro[4.5]decanedione, dialkylglutarimide, thiazolidinedione, spirocyclopentylthiazolidinedione, or morpholine-2,6-dione. The compounds have psychotropic properties and 2-[4-[4-(2,4-dioxo-1-thia-3-azaspiro[4.5]nonane-3-yl)butyl]-1-piperazinyl]pyridine-3-carboxaldehyde is a typical embodiment having selective antipsychotic activity.

9 Claims, No Drawings

ANTIPSYCHOTIC CYCLIC IMIDE DERIVATIVES OF 2-(4-BUTYLPIPERAZIN-1-YL)PYRIDINES, COMPOSITIONS AND USE

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is a substituted pyridin-2-yl ring, generally with a substituent in the 3-position of the ring; and the other is a butylene chain bearing a cyclic imide ring moiety at its terminus. Examples of these cyclic imide heterocycles are depicted below:

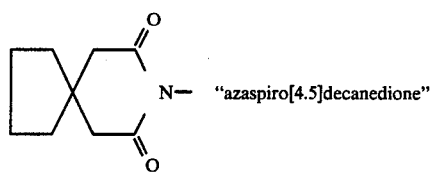

"azaspiro[4.5]decanedione"

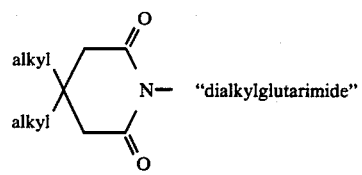

"dialkylglutarimide"

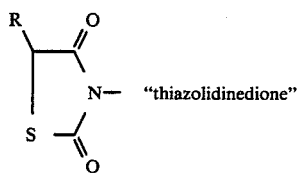

"thiazolidinedione"

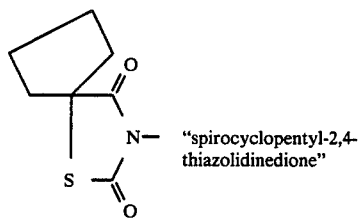

"spirocyclopentyl-2,4-thiazolidinedione"

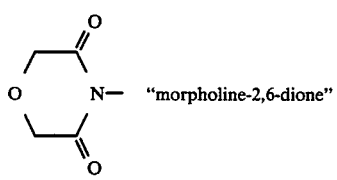

"morpholine-2,6-dione"

A considerable amount of related art has accumulated over the past 10 years. The more pertinent related art may be viewed in light of the following general structural formula (1)

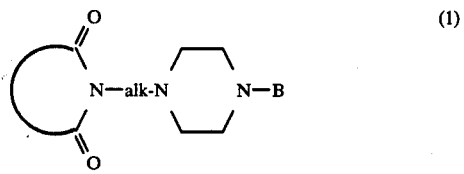

in which alk is an alkylene chain connecting the piperazine ring and the cyclic imide group and B is a heterocyclic ring with optional substituents.

Wu, et al, U.S. Pat. Nos. 3,717,634, 3,907,801 and a corresponding Wu, et al, publication—*J. Med. Chem.*, 15, 447–479 (1972)—describe various azaspiro[4.5]decanedione psychotropic compounds wherein B represents various heterocycles such as pyridine, pyrimidine, or triazine, all with optional substituents. Specifically B can be, inter alia,

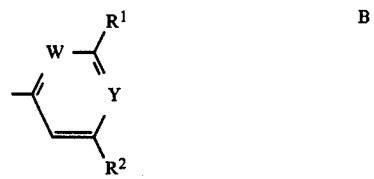

wherein one of W and Y is CH and the other is nitrogen; $R^1$ and $R^2$ are independently selected from hydrogen, lower ($C_1$–$C_6$) alkyl or lower alkoxy. As can be seen, B cannot be a 3-substituted pyridin-2-yl moiety, as in the instant invention.

Temple, et al, in U.S. Pat. No. 4,305,944 disclose azaspiro[4.5]decanedione tranquilizing compounds wherein B is a 3-cyanopyridin-2-yl or 3-methoxypyridin-2-yl moiety or dialkylglutarimide tranquilizing compounds wherein B is a 3-cyanopyridin-2-yl ring with halogen or trifluoromethyl as a second substituent on the pyridine ring.

Temple and Yeager in U.S. Pat. Nos. 4,367,335 and 4,456,756 disclose thiazolidinediones and spirothiazolidinediones wherein B is a 2-pyridine radical, either unsubstituted or containing a cyano substituent.

A preferred compound of this series is known as MJ 13980, formula (2),

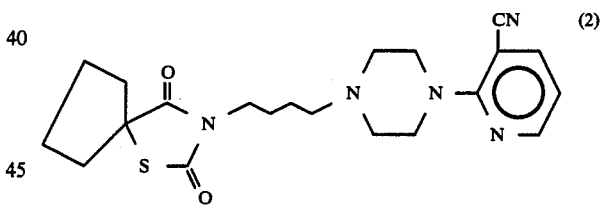

but was found to have toxicological problems prior to clinical testing. Specifically, adrenal hypertrophic changes were associated with chronic administration of MJ 13980. Examination of the molecular structure of MJ 13980 suggests that the cyanopyridine moiety is a likely suspect as the pharmacophore which may be responsible for the unwanted toxicological effect.

While the psychotropic compounds listed above are generally related to the compounds of the instant invention, they are nonetheless distinguishable therefrom on both specific structural as well as pharmacological grounds. Essentially, in the art compounds, B is either unsubstituted or bears a cyano group usually in the 3-position. This differs from the present compounds which have no cyano group and are generally substituted in the 3-position.

SUMMARY AND DETAILED DESCRIPTION OF THE INVENTION

In its broadest aspect, the present invention is concerned with piperazinyl derivatives having neuroleptic (antipsychotic) properties characterized by a compound of Formula I

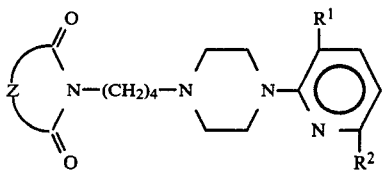

and its pharmaceutically acceptable acid addition salts. In Formula I Z represents the radicals

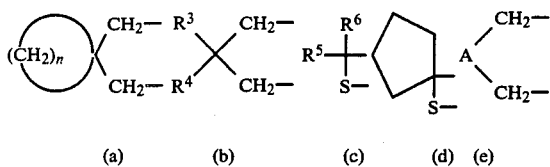

in which n is the integer 3 to 6; $R^3$ and $R^4$ are independently lower alkyl of 1 to 4 carbon atoms; and $R^5$ and $R^6$ are independently chosen from hydrogen, lower alkyl of 1 to 4 carbon atoms, or phenyl; and A is an oxygen or sulfur atom. $R^1$ is selected from among hydrogen, lower alkyl, lower alkoxy, formyl, carbalkoxy, halogen, nitro, phenyl, or

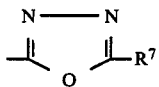

wherein $R^7$ is lower alkyl. $R^2$ is chosen from among hydrogen, halogen, lower alkyl, lower alkoxy, but with the proviso that $R^1$ and $R^2$ cannot both be hydrogen.

The term "lower alkyl" as used herein refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, and 2-methylpropyl.

There are two classes of preferred compounds. In class 1, $R^2$ is hydrogen and $R^1$ is as defined except for hydrogen; and Z is as defined above. In class 2, $R^2$ is other than hydrogen, $R^1$ is as defined, and Z is as defined except (a). The most preferred compounds comprise Z as defined; $R^1$ selected from among formyl, carbalkoxy, and nitro; and $R^2$ being hydrogen.

The pharmaceutically acceptable acid addition salts of the invention are those in which the anion does not contribute significantly to the toxicity or pharmacological activity of the salt and, as such, they are the pharmacological equivalents of the bases of Formula I. They are generally preferred for medical usage. In some instances, they have physical properties which make them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with a selected acid preferably by contacting solutions employing an excess of commonly used inert solvents such as ether, water, benzene, ethanol, ethyl acetate, and acetonitrile. The salt form may also be prepared by any of the other standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid, and the like; useful inorganic acids are hydrohalide acids such as HCl, HBr, HI; sulfuric acids; phosphoric acid; and the like.

It is also to be understood that the present invention is considered to include any stereoisomers which may result when, for example, Z is (b) or (c). Separation of the individual stereoisomers may be accomplished by application of various methods which are well known to practitioners in the art.

The compounds of the instant invention are useful pharmacological agents with psychotropic properties. In this regard, they exhibit selective central nervous system activity at non-toxic doses and are of particular interest as neuroleptic (antipsychotic) agents. As with other known antipsychotics, the compounds of Formula I evoke certain responses when studied in standard in vivo and in vitro pharmacological tests systems which are known to correlate well with the relief of symptoms of acute and chronic psychosis in man.

As indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of the compound's ability to affect corresponding central nervods system function or cause side effects in vivo. This principle is employed in a test measuring inhibition of [$^3$H]spiperone binding which indicates significant dopamine receptor binding activity (cf: Burt, et al., Molecular Pharmacology, 12, 800 (1976); Science, 196, 326 (1977); Creese, et al., Science, 192, 481 (1976)).

The following in vivo test systems are illustrative of the conventional testing used to classify and differentiate a psychotropic agent from a non-specific CNS depressant and determine potential side-effect liabilities such as cataleptic activity.

TABLE 1

In Vivo Tests Used to Evaluate Formula I Compounds

1. Conditioned Avoidance Response (CAR)—measure of a drug's tranquilizing activity as determined by its attenuation of avoidance response to electrical shock in trained fasted rats. cf: Albert, Pharmacologist, 4, 152 (1962); Wu, et al, J. Med. Chem., 12, 876–881 (1969).
2. Inhibition of Apomorphine-Induced (APO) Stereotypy—an assessment of blockade of dopaminergic activity in rats as measured by attenuation of the behavioral syndrome caused by the dopamine agonist, apomorphine. cf: Janssen, et al, Arzneimittel. Forsch., 17, 841 (1966).
3. Catalepsy—drug-induced catalepsy in rats is predictive of potential extrapyramidal symptoms (EPS) in man. cf: Costall, et al, Psychopharmacologia, 34, 233–241 (1974); Berkson, J. Amer. Statist. Assoc., 48, 565–599 (1953).
4. Catalepsy Reversal—measure of a drug's ability to reverse neuroleptic-induced catalepsy in the rat.

According to the pharmacological profile established by the aforementioned tests, the instant compounds of Formula I have promising antipsychotic potential in that they are relatively potent in the CAR test having oral $ED_{50}$ values $<100$ mg/kg body weight and $IC_{50}$'s of $<1000$ nanomolar in the [$^3$H]spiperone dopamine receptor binding assay. Activity in the CAR test and spiperone assay is considered predictive of antipsychotic potential in man. Regarding selective antipsychotic activity, preferred compounds of the invention have significant dopamine receptor binding activity and suppress rat CAR below cataleptic doses. Concerning side effect liability, the instant compounds are relatively inactive in catalepsy production and, even more significantly, preferred compounds of the invention demonstrate the ability to reverse neuroleptic-induced catalepsy with $ED_{50}$ values of $<20$ mg/kg, given orally. The significance of the effects of compounds of the instant invention on catalepsy induction and reversal are better appreciated when one considers that antipsychotic agents as a class are known to produce sedation and extrapyramidal reactions. These extrapyramidal reactions are comprised of acute torsion dystonia, akathisia, Parkinsonism, tardive dyskinesia, and autonomic nervous system effects.

In summary of the foregoing discussion, the instant compounds have psychotropic properties particularly suited to their use as neuroleptic (antipsychotic) agents. Thus, another aspect of the instant invention concerns a process for ameliorating a psychotic state in a mammal in need of such treatment which comprises systemic administration to such mammal of an effective dose of Formula I compound or a pharmaceutically acceptable acid addition salt thereof.

The administration and dosage regimen of compounds of Formula I is considered to be done in the same manner as for the reference compound clozapine, cf: *The Merck Index*, 10th Edition, (1983), page 344, and references therein. Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 10 mg/kg, preferably, 0.1 to 2 mg/kg, when administered parenterally; and from about 1 to about 50 mg/kg, preferably 2 to 30 mg/kg, when administered orally. In some instances, a sufficient therapeutic effect can be obtained at lower doses while in others, larger doses will be required. The term systemic administration as used herein refers to oral, rectal, and parenteral, i.e., intramuscular, intravenous, and subcutaneous routes. Generally, it will be found that when a compound of the present invention is administered orally which is the preferred route, a larger quantity of the active agent is required to produce the same effect as a smaller quantity given parenterally. In accordance with good clinical practice, it is preferred to administer the instant compounds at a concentration level that will produce effective neuroleptic (antipsychotic) effects without causing any harmful or untoward side effects.

Therapeutically, the instant compounds are generally given as pharmaceutical compositions comprised of an effective antipsychotic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with a pharmaceutical carrier, the carrier comprising one or more solids, semi-solid, or liquid diluent, filler and formulation adjuvant which is non-toxic, inert and pharmaceutically acceptable. Such pharmaceutical compositions are preferably in dosage unit forms; i.e., physically discrete units containing a pre-determined amount of the drug corresponding to a fraction or multiple of the dose which is calculated to produce the desired therapeutic response. The dosage units can contain 1, 2, 3, 4, of more single doses, or alternatively, $\frac{1}{2}$, $\frac{1}{3}$, or $\frac{1}{4}$ of a single dose. A single dose preferably contains an amount sufficient to produce the desired therapeutic effect upon administration at one application of one or more dosage units according to the pre-determined dosage regimen, usually a whole, half, third, or quarter of the daily dosage administered once, twice, three or four times a day. Other therapeutic agents can also be present. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethylene glycols or mixtures thereof. The polyethylene glycols consist of a mixture of nonvolatile, usually liquid, polyethylene glycols which are soluble in both water and organic liquids and which have molecular weights of from about 200 to 1500.

The compounds of Formula I wherein Z is the divalent radical (a-e) of the instant invention are obtained by procedures involving alkylation of piperazinyl or "imide" intermediates analogous to the methods described by Wu, et al., patents supra., or Temple, et al., patents, supra., all incorporated herein in entirety by reference. These methods may be incorporated into a unitary process which is employed for preparation of the compounds of Formula I. The methods may be adapted to variation in order to produce other compounds embraced by this invention but not specifically disclosed. Further, variations of the methods to produce the same compounds in somewhat different fashion will also be evident to one skilled in the art. Certain examples will be given for specific illustration.

Unitary Process

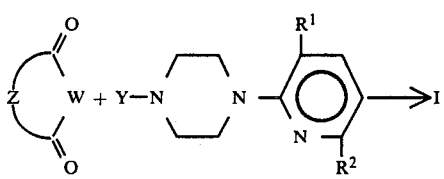

In this scheme, $R^1$, $R^2$, and Z have the same meanings as previously assigned to them in Formula I. The symbol "W" can be $>O$; $>NH$; or $>N-(CH_2)_4-X$. The symbol "Y" can be $H_2N-(CH_2)_4-$; $X-(CH_2)_4-$;

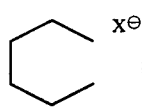

or H. The relationship between W and Y is:

| Method No. | A | B | C |
|---|---|---|---|
| when W is: | $>O$ (IIa) | $>NH$ (IIb) | $>N-(CH_2)_4-X$ (IIc) |
| then Y is: | $H_2N-(CH_2)_4-$ (IIIa) | $X-(CH_2)_4-$ (IIIb) or [cyclic]$X^\ominus$ (IIIb') | H (IIIc) |

The symbol "X" refers to a suitable displacement group such as chloride, bromide, iodide, sulfate, phosphate, tosylate, or mesylate.

Method A

Method B

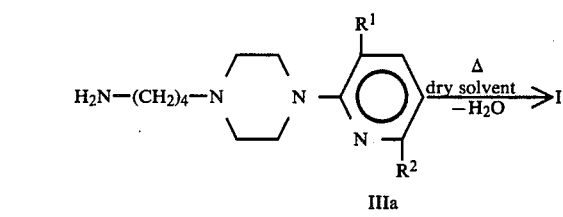

(1)

-continued

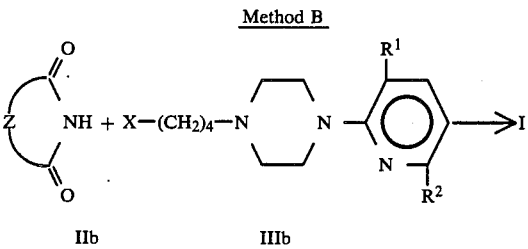

(2)

Method C (the preferred method)

The condensation process in Method A is carried out by refluxing the reactants in a dry, inert reaction medium such as pyridine or xylene. For Methods B and C the process is carried out under reaction conditions suitable for the preparation of tertiary amines by alkylation of secondary amines. The reactants are heated in a suitable organic liquid at temperatures of about 60° to about 150° C. in the presence of an acid binding agent. Benzene, dimethylformamide, ethanol, acetonitrile, toluene and n-butyl alcohol are preferred examples of the organic liquid reaction media. The preferred acid binding agent is potassium carbonate, but other inorganic and tertiary organic bases may be employed including other alkali and alkaline earth metal carbonates, bicarbonates, or hydrides, and the tertiary amines. All three methods have been adequately described in the patent references referred to hereinabove as being incorporated in entirety by reference. For the compounds of the instant invention, Method C is the preferred synthetic process. The required IIc intermediates were synthesized according to methods given in the incorporated reference patents.

As an example of a method variation to produce the same compounds somewhat differently, an N-substituted [4-(1-piperazinyl)butyl]cyclic imide (IV) can be reacted with an appropriate pyridine system (V) to yield a product of Formula I, e.g.

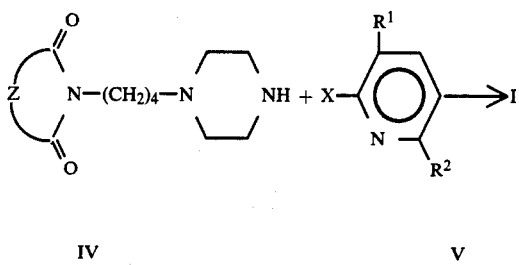

IV    V

Additionally, a Formula I compound can undergo a further chemical alteration of its $R^1$-group (e.g. conversion of a formyl group to an oxime or related compound) to yield a different Formula I product.

The intermediate cyclic imide compounds of Formula II or IV are adequately described in the incorporated above-cited patent references, references therein, and several Formula II compounds are commercially available. The pyridinylpiperazine intermediate compounds of Formula III, as well as the starting pyridines, are either commercially available, found in the chemical literature, or described herein. Methods used for the synthesis of III intermediates are illustrated in Scheme 1.

acetic anhydride. In some cases, the pyridones (VIII) can also be formed by electrophilic ring closure of an alicyclic isocyanate precursor formed from the corresponding acid azide (IX) by the Curtius rearrangement. Treatment of pyridones formed through either approach with phosphorus oxychloride supplies the corresponding 2-chloropyridines (VI). These chloropyridines may also be prepared beginning with chloropyridines of structure VII wherein the Y group is appropriately modified to give the desired $R^1$ group. Examples would be: treatment of the sodium salt of 2-chloro-3-pyridinol (Y=OH) with iodomethane in DMSO at room temperature; a DIBAL-H reduction of 2-chloro-3-cyanopyridine (Y=CN) at $-70°$ C., followed by acid hydrolysis affords 2-chloropyridine-3-carboxaldehyde; 2-chloronicotinic acid (Y=COOH) is esterified using diazomethane to give the carbomethoxy VI intermediate.

Reaction of these substituted 2-chloropyridines (VI) with a five-fold excess of piperazine in either refluxing isopropanol for variable periods of time, or neat in a sealed bomb for 24 hours at 120° C. will yield IIIc intermediates which may be further converted, for example, into IIIb by treatment with 1,4-dibromobutane or, treated with 3-bromobutyronitrile to give XII which may be then reduced to IIIa.

Scheme 1
Synthesis of Pyridine Intermediate

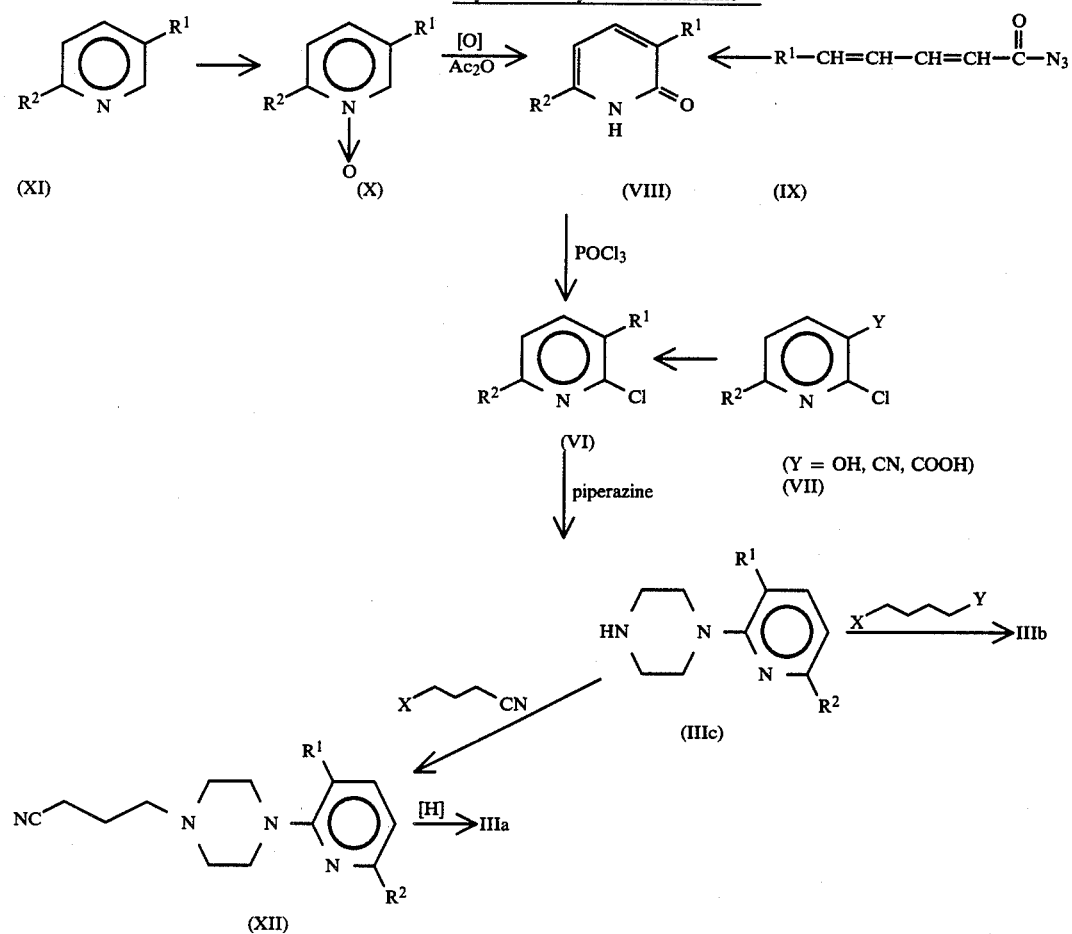

As shown in Scheme 1, pyridines (XI) may be converted to the corresponding 2(1H)-pyridone (VIII) by treatment of the N-oxide (X) with hydrogen peroxide in

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C. when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton (DMR) spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), triplet (t), or quartet (q). Abbreviations employed are DMSO-$d_6$ (perdeuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. All compounds gave satisfactory elemental analyses.

Synthesis of Intermediates of Formula IIIc

The following examples illustrate synthesis of the key intermediate IIIc, which can be further converted using known reactions as in the cited patents, into other synthetic intermediates.

EXAMPLE 1

1-(3-Phenyl-2-pyridinyl)piperazine

A mixture of 3-phenylpyridine (XI; 100.0 g, 0.64 mole) and glacial acetic acid (400 mL) was treated dropwise with 30% hydrogen peroxide (65 mL) at room temperature. The solution was gradually heated to 75° for 1.5 hr. and treated with additional hydrogen peroxide (75 mL). The reaction mixture was concentrated in vacuo and Kugelrohr distillation (145°–160°/0.1 Torr.) gave a quantitative yield of 110 g of an oil (X). The N-oxide oil (X) was dissolved in acetic anhydride (400 mL) and heated at reflux under nitrogen for 24 hrs. The reaction mixture was concentrated in vacuo, dissolved in methylene chloride and extracted with water (4×250 mL). The organic layer was isolated, dried (Na$_2$SO$_4$), filtered, and concentrated in vacuo to a solid which was recrystallized from ethyl acetate to afford 60.3 g (45%) of 3-phenyl-2-(1H)-pyridone (VIII), m.p. 223°–229°.

A solution of 3-phenyl-2-(1H)-pyridone (VIII; 20.0 g, 0.12 mole) and phosphorus oxychloride (300 mL) was refluxed for 6 hr and then slowly poured over crushed ice (300 mL). The resulting solution was made basic with ammonium hydroxide which led to formation of a precipitate. The mixture was extracted with ethyl ether (3×500 mL) and the combined organic extracts were dried (Na$_2$SO$_4$). Concentration in vacuo gave a solid which was recrystallized from ethyl acetate to yield 7.0 g (31%) of 2-chloro-3-phenylpyridine (VI), m.p. 52°–56°.

A neat mixture of 2-chloro-3-phenylpyridine (VI; 28.8 g, 0.15 mole) and piperazine (65.7 g, 0.76 mole) was heated for 24 hr at 165° in a sealed bomb. The cooled mixture was partitioned between methylene chloride and water, the organic phase was further extracted with water (3×300 mL), isolated, dried (MgSO$_4$), filtered, and concentrated in vacuo producing an oil. Flash chromatography (15% ethanol-chloroform) and concentration in vacuo of the appropriate fractions yielded an oil which was dissolved in ethanol and treated with 1 equivalent of ethanolic HCl. The hydrochloride salt precipitated upon cooling to give 19.8 g (48.2%) of the IIIc intermediate as a white hydrochloride salt, m.p. 185°–187°.

EXAMPLE 2

1-(3-Methyl-2-pyridinyl)piperazine

A solution of 2,4-hexadienoic acid (190.0 g, 0.7 mole) and triethylamine (202.1 g, 2.0 mole) in acetone (1.5 L) was treated dropwise with a mixture of ethylchloroformate (216.3 g, 2.0 mole) in acetone (500 mL) at 0°. The reaction mixture was stirred for 0.75 hr at 0° and then treated dropwise with a solution of sodium azide (169.0 g, 2.6 mole) in water (700 mL). After being stirred for 1 hr at 0°, the reaction mixture was poured into water (800 ml) and extracted with methylene chloride (3×400 mL). The combined organic extracts were dried (Na$_2$SO$_4$), filtered and concentrated in vacuo to yield the crude acid azide (IX). A solution of acid azide (IX) in methylene chloride (200 mL) was cautiously added dropwise to an oversized 3-neck round bottom flask which was equipped with two air condensers and contains phenyl ether heated at 220°–240°. Once addition is completed, the reaction mixture was heated 1 hr and the phenyl ether removed by Kugelrohr distillation (170°–180°/0.1 Torr.). The contents of the still pot were recrystallized from benzene to yield 61.2 g (33%) of 3-methyl-2-(1H)-pyridone (VIII) as white crystals.

Using the procedure given above in Example 1, 3-methyl-2(1H)-pyridone (VIII) was refluxed in phosphorus oxychloride followed by work-up to give a 17% yield of 2-chloro-3-methylpyridine (VI).

Reaction of the 2-chloro-3-methylpyridine with piperazine in a sealed bomb further using the procedure of Example 1 above resulted in a 50% yield of the desired IIIc product.

EXAMPLE 3

2-(1-Piperazinyl)pyridine-3-carboxaldehyde

A solution of 2-chloro-3-cyanopyridine (VII; 2.0 g, 0.01 mole) in methylene chloride was treated dropwise with a 1M solution of DABAL-H in methylene chloride (0.03 mole, 33 mL) at −78°. The solution turned from a colorless to a bright yellow-orange color during the addition, and the stirring was continued for 3 hr at −78°. The mixture was treated with 3N HCl (75 mL) which rapidly warmed the reaction to −10°. The rate of addition was regulated so as to maintain the reaction temperature below 0°. The solution was treated dropwise with 10% sodium hydroxide solution which formed a bright yellow emulsion which was filtered through sintered glass. The collected aluminum salts were exhaustively washed with methylene chloride, filtered, and the filtrate dried (MgSO$_4$). Concentration of the organic solution in vacuo gave a yellow solid which was purified by Kugelrohr distillation (60°/0.4 Torr.) affording 0.46 g (33%) of 2-chloro-3-pyridinecarboxaldehyde (VI) as a white solid, m.p. 48°.

A solution of 2-chloro-3-pyridinecarboxaldehyde (VI; 6.4 g, 0.05 mole) and piperazine (19.4 g, 0.23 mole) was refluxed 5 hr in isopropanol (250 mL). The reaction mixture was concentrated in vacuo to a syrup which was partitioned between methylene chloride and water. The organic phase was isolated, washed with water (3×500 mL), dried (MgSO$_4$), filtered, and concentrated in vacuo to a syrup which was flash chromatographed (10% methanol-methylene chloride). The appropriate fractions were combined, concentrated in vacuo, dissolved in ethanol and treated with 1 equivalent of ethanolic HCl. Crystallization of the crude hydrochloride salt gave 8.8 g (87%) of the appropriate IIIc intermediate.

EXAMPLE 4

1-(3-Methoxy-2-pyridinyl)piperazine

A solution of sodium (3.2 g, 0.14 mole) in methanol (40 mL) was treated with 2-chloro-3-pyridinol (VII; 18 g, 0.14 mole) and refluxed for 0.5 hr. Dry dimethylsulfoxide was added dropwise until the reaction mixture clarified, and the solution was concentrated in vacuo. The collected foam was dissolved in dimethylsulfoxide (50 mL) and heated with iodomethane (19.9 g, 0.14 mole) at room temperature which led to formation of a precipitate. The precipitate was collected by filtration and subjected to Kugelrohr distillation (68°/0.5 torr.) yielding white crystals (28.5 g). The solid was partitioned between ether and water, the organic phase isolated, dried (Na$_2$SO$_4$), filtered, and concentrated in vacuo affording 4.3 g (21%) of white crystalline 2-chloro-3-methoxypyridine (VI).

The 2-chloro-3-methoxypyridine (VI) was treated with piperazine in a refluxing isopropanol medium according to the procedure of Example 3 and, following a similar work-up, gave the desired IIIc intermediate.

EXAMPLE 5

Methyl 2-(1-Piperazinyl)pyridine-3-carboxylate

A stirred solution of potassium hydroxide (22.6 g, 0.4 mole), ethanol (45.3 mL), and water (36 mL) was treated with N-methyl N-nitroso-p-toluenesulfonamide (22.6 g, 0.1 mole; Diazald ®-Aldrich) in ether (204 mL) at 65°. The rate of addition of the solution was regulated by the rate of distillation of the ether diazomethane solution. A diazomethane generation kit containing all polished glass surfaces was used to distill the ethanol diazomethane solution which was received in two collection vessels connected in tandem, the first cooled to 0° and the second to −78°. The combined diazomethane solutions were treated dropwise with the solution of 2-chloronicotinic acid (4.7 g, 0.03 mole) in methanol at −15°. The reaction mixture was maintained at −15° for 4 hr and then slowly allowed to equilibrate to room temperature. The solution was concentrated in vacuo to a yellow solid, partitioned between aqueous sodium carbonate and methylene chloride, and the organic layer was isolated, dried (MgSO$_4$), and concentrated in vacuo to yield 5.2 g (approximately 100%) of methyl 2-chloronicotinate (VI) as a crude oil suitable for reaction with piperazine as given below.

A mixture of methyl 2-chloronicotinate (VI, 3.8 g, 0.02 mol) and piperazine (9.7 g, 0.11 mol) were refluxed in isopropanol for 24 hours. The solution was concentrated in vacuo, partitioned between dichloromethane and water and the organic layer was isolated, dried (MgSO$_4$), and concentrated in vacuo to a golden oil. This oil was subjected to flash chromatography (CH$_2$Cl$_2$-10% MeOH-1% NH$_4$OH), and the appropriate portions were combined and concentrated in vacuo to yield pure IIIc product as a golden oil (1.7 g, 35%). NMR and IR spectral data were consistent with the assigned structure.

EXAMPLE 6

1-(3-Nitro-2-pyridinyl)piperazine

A mixture of 2-chloro-3-nitropyridine (VI; 2.5 g, 0.015 mole) and piperazine (6.5 g, 0.075 mole) was stirred for 30 minutes in isopropanol (100 mL) at room temperature. The solution was concentrated in vacuo, partitioned between dichloromethane and water, and the organic layer was isolated, dried (MgSO$_4$), and concentrated in vacuo to an orange oil. The oil was dissolved in a minimum volume of isopropanol which upon chilling and filtration yielded a yellow solid IIIc product (3.1 g, 96.5%), m.p. 82°–85° C.

Anal. Calcd. for C$_9$H$_{12}$N$_4$O$_2$: C, 51.91; H, 5.80; N, 26.90. Found: C, 52.21; H, 5.83; N, 26.95.

EXAMPLE 7

1-[3-(5-Methyl-1,3,4-oxadiazol-2-yl)-2-pyridinyl]piperazine

This intermediate compound was synthesized from 2-chloro-3-(5-methyl-1,3,4-oxadiazol-2-yl)pyridine (prepared according to *J. Heterocyclic Chemistry*, 17, 425 (1980)) and piperazine using the procedure of Example 6.

By selection of the appropriate starting materials and use of suitable procedures as outlined in the above examples, other required IIIc intermediates would be readily available to one skilled in the art of chemical synthesis.

Synthesis of Products of Formula I

The synthetic methods which have been outlined hereinabove for preparation of I compounds are adequately describe and exemplified in the cited patents which have been incorporated by reference. For convenience, a general procedure and some specific examples for use of the preferred method (Method C) are given below.

EXAMPLE 8

N-[4-[4-(3-Substituted-2-pyridinyl)-1-piperazinyl]-butyl]-cyclic imino Derivatives (General Method)

The following experimental conditions represent the general procedure employed in the synthesis of the compounds of Formula I. A mixture of the appropriate N-(4-bromobutyl)-cyclic imino compound (e.g. 5-spirocyclopentyl-2,4-thiazolidinedione, 8-spiro[4.5]decane-7,9-dione, 4,4-dialkyl-2,6-piperidinedione, or N-morpholine-2,6-dione, all with attached 4-bromobutyl chain; 1 equivalent), a 1-(3-substituted-2-pyridinyl)piperazine derivative (IIIc; 1 equivalent), and potassium carbonate (3 equivalents) was refluxed for variable periods of time (4–24 hr) in acetonitrile. The reaction mixture was filtered, concentrated in vacuo, and flash chromatographed, usually in a solvent mixture of ethanol-chloroform. Concentration in vacuo of the appropriate chromatographic fractions, dissolution in an organic solvent, and treatment with ethanolic hydrochloric acid led to isolation of the Formula I compounds as their hydrochloride salts.

EXAMPLE 9

2-[4-[4-(3-Nitro-2-pyridinyl)-1-piperazinyl]butyl]-1-thia-3-azaspiro[4.4]nonane-2,4-dione A mixture of 3-(4-bromobutyl)-5-spirocyclopentyl)-2,4-thiazolidinedione (IIc; 5.5 g, 0.018 mole), 1-(3-nitro-2-pyridinyl)piperazine (IIIc, prepared in Ex. 6; 3.75 g, 0.018 mole), and potassium carbonate (4.9 g, 0.036 mole) was refluxed in acetonitrile (300 mL) for 24 hr. The solution was filtered, concentrated in vacuo, and flash chromatographed ($CHCl_3$-4% EtOH) to yield 5 g (64%) of an orange oil. Treatment of a chilled acetonitrile solution of this oil with ethanolic hydrochloric acid yielded the yellow dihydrochloride salt, m.p. 190°–194° C.

Anal. Calcd. for $C_{20}H_{27}N_5O_4S\cdot2HCl$: C, 47.44; H, 5.77; N, 13.83. Found: C, 47.69; H, 5.69; N, 14.19.

NMR (DMSO-$d_6$): 1.75 (8,m); 2.23 (4,m); 3.11 (4,m); 3.59 (8,m); 7.06 (1,dd, 4.2, 8.0 Hz); 8.36 (1,dd, 1.4, 8.0 Hz); 8.49 (1,dd, 1.4, 4.2 Hz); 11.85 (1,bs); 11.90 (1,bs).

IR (KBr): 945, 1340, 1440. 1535, 1595, 1635, 1675, 1740, 2430, 2950.

EXAMPLE 10

2-[4-[4-(2,4-Dioxo-1-thia-3-azaspiro[4.4]nonan-3-yl)butyl]-1-piperazinyl]pyridine-3-carboxaldehyde Hydrochloride A mixture of 3-(4-bromobutyl)-5-spirocyclopentyl)-2,4-thiazolidinedione (IIc; 5.5 g, 0.018 mole), 2-(1-piperazinyl)pyridine-3-carboxaldehyde (IIIc, prepared in Ex. 3: 3.4 g, 0.018 mole), and potassium carbonate (4.9 g, 0.036 mole) was refluxed in acetonitrile (100 mL) for 24 hr. The solution was filtered, concentrated in vacuo, and flash chromatographed ($CH_2Cl_2$-5% MeOH) to yield a brown oil. The brown oil was dissolved in hot acetonitrile and heated with ethanolic hydrochloric acid affording a white solid after chilling and filtration (2.8 g, 3.7%), m.p. 187°–189° C.

Anal. Calcd. for $C_{21}H_{28}N_4O_3S\cdot HCl$: C, 55.68; H, 6.45; N, 12.37. Found: C, 55.96; H, 6.55; N, 12.43.

NMR ($CDCl_3$): 2.04 (2,m); 3.35 (6,m); 3.69 (2,t, 6.7 Hz); 3.95 (4,m); 7.06 (1,dd, 4.5, 7.7 Hz); 8.07 (1,dd, 1.8, 7.7 Hz); 8.41 (1,dd, 1.8, 4.5 Hz); 10.02 (1,s); 11.80 (1,bs).

IR (KBr): 940, 1350, 1365, 1390, 1435, 1580, 1675, 1745, 2590, 2950.

EXAMPLE 11

Methyl 2-[4-[4-(2,4-Dioxo-1-thia-3-azaspiro[4.4]nonan-3-yl)butyl-1-piperazinyl]pyridine-3-carboxylate Dihydrochloride A mixture of 3-(4-bromobutyl)-5-spirocyclopentyl-2,4-thiazolidinedione (IIc; 3.5 g, 0.011 mole), methyl 2-(1-piperazinyl)-3-pyridinecarboxylate (IIIc, prepared in Ex. 5; 2.5 g, 0.011 mole) and 3.1 g (0.022 mole) of potassium carbonate were refluxed in acetonitrile (300 mL) for 24 hr. The solution was filtered and concentrated in vacuo to a dark viscous oil which was flash chromatographed ($CHCl_3$-5% EtOH) yielding a golden oil. The oil was dissolved in hot acetonitrile and treated with ethanolic hydrochloric acid to generate the hydrochloride salt (2.04 g, 40.8%), m.p. 195° C.

Anal. Calcd. for $C_{22}H_{30}N_4O_4S\cdot2HCl$: C, 50.87; H, 6.21; N, 10.74. Found: C, 50.71; H, 6.37; N, 10.76.

NMR (DMSO-$d_6$): 1.76 (8,m); 2.20 (4,m); 3.10 (4,m); 3.55 (6,m); 3.83 (3,s); 3.90 (2,m); 7.00 (1,dd, 4.8, 7.4 Hz); 8.11 (1,dd, 1.6, 7.4 Hz; 8.16 (2,bs); 8.35 (1,dd, 1.6, 4.8 Hz); 11.70 (1,bs).

IR (KBr): 770, 1270, 1350, 1600, 1670, 1725, 2370, 2950.

Some additional examples of Formula I products prepared by means of these above synthetic procedures are listed in Table 2.

TABLE 1

Formula I Compounds

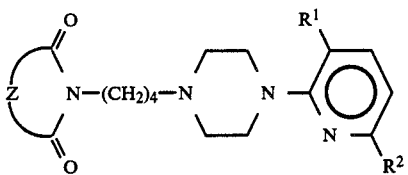

| Ex. | $Z^{(a)}$ | $R^1$ | $R^2$ | Formula | m.p. (°C.) |
|---|---|---|---|---|---|
| 12 | (d) | —OMe | H | $C_{21}H_{30}N_4O_3S\cdot C_7H_8SO_3$ | 125–128 |
| 13 | (d) | —Me | H | $C_{21}H_{30}N_4O_2S\cdot HCl$ | 175–182 |
| 14 | (b) | —Me | H | $C_{21}H_{32}N_4O_2\cdot1.1HCl$ | 195–200 |
| 15 | (b) | —Cl | H | $C_{20}H_{29}ClN_4O_2\cdot1.2HCl$ | 217–221 |
| 16 | (d) | —Cl | H | $C_{20}H_{27}ClN_4O_2S\cdot HCl$ | 185–188 |
| 17 | (d) | —Ph | H | $C_{26}H_{32}N_4O_2S\cdot C_4H_4O_4\cdot0.4H_2O$ | 125–127 |
| 18 | (a) | —OMe | H | $C_{23}H_{34}N_4O_3\cdot2HCl$ | 194–196 |
| 19 | (e) | —Ph | H | $C_{23}H_{28}N_4O_3\cdot2.1HCl\cdot H_2O$ | 225–235(d) |
| 20 | (a) | —Me | H | $C_{23}H_{34}N_4O_2\cdot2HCl\cdot1.3H_2O$ | 145–147 |
| 21 | (b) | —Ph | H | $C_{26}H_{34}N_4O_2\cdot1.2HCl\cdot0.8H_2O$ | 230–235 |
| 22 | (d) | H | —OMe | $C_{21}H_{30}N_4O_3S\cdot HCl$ | 194–196 |
| 23 | (b) | H | —OMe | $C_{21}H_{32}N_4O_3HCl$ | 212–214 |
| 24 | (e) | —Cl | H | $C_{17}H_{23}ClN_4O_3\cdot2HCl$ | 217–220 |
| 25 | (e) | —CHO | H | $C_{18}H_{24}N_4O_4\cdot HCl$ | 184–186 |
| 26 | (e) | —$NO_2$ | H | $C_{17}H_{23}N_5O_5\cdot HCl$ | 199–203 |
| 27 | (b) | —$CO_2Me$ | H | $C_{22}H_{32}N_4O_4\cdot HCl$ | 168–171 |
| 28 | (d) | —CH=NOMe | H | $C_{22}H_{31}N_5O_3S\cdot HCl$ | 168–170 |
| 29 | (e) | —$CO_2Me$ | H | $C_{19}H_{26}N_4O_5\cdot2HCl$ | 185–187 |
| 30 | (a) | 5-methyl-1,3,4-oxadiazol- | H | $C_{25}H_{34}N_6O_3\cdot HCl\cdot0.5H_2O$ | 185–187 |

TABLE 1-continued
Formula I Compounds
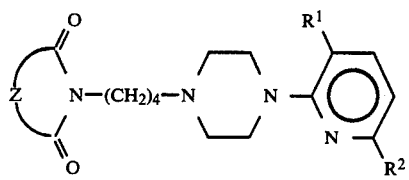
| Ex. | Z(a) | R¹ | R² | Formula | m.p. (°C.) |
|---|---|---|---|---|---|
|  |  | 2-yl |  |  |  |
(a)Z is
(a) 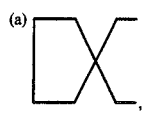,
(b) 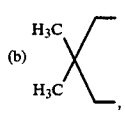,
(c) ,
(d) 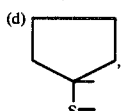,
(e) 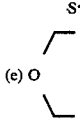
TABLE 3
Additional Formula I Compounds
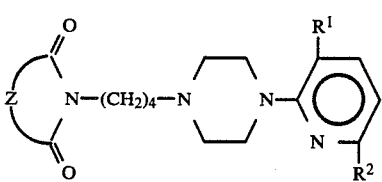  I
| Ex. | Z | R¹ | R² |
|---|---|---|---|
| 31 |  | H | —OMe |
| 32 |  | CHO | H |
| 33 |  | CO₂Me | H |
| 34 | 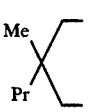 | CHO | Cl |
TABLE 3-continued
Additional Formula I Compounds
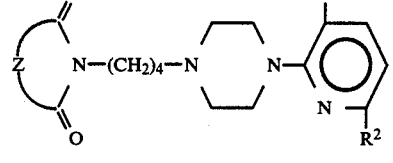  I
| Ex. | Z | R¹ | R² |
|---|---|---|---|
| 35 |  | NO₂ | H |
| 36 |  | H | OMe |
| 37 |  | CHO | H |
| 38 |  | CHO | Cl |

TABLE 3-continued

Additional Formula I Compounds

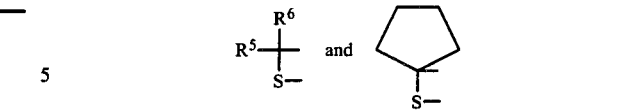

| Ex. | Z | R¹ | R² |
|---|---|---|---|
| 39 | 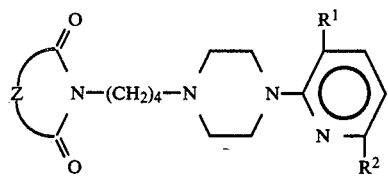 | CHO | H |

What is claimed is:

1. A compound of Formula I

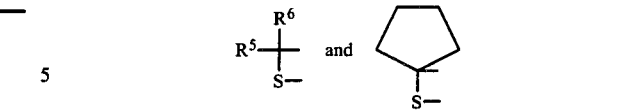

and the pharmaceutically acceptable acid addition salts thereof wherein

R¹ is selected from formyl and carbalkoxy

R² is selected from hydrogen, halogen, lower alkyl, or lower alkoxy

Z is selected from

$R^5$ and $R^6$ are independently chosen from hydrogen, lower alkyl, or phenyl.

2. A compound of claim 1 wherein Z is

with $R^5$ and $R^6$ being independently chosen from hydrogen, lower alkyl, or phenyl.

3. A compound of claim 1 wherein Z is

4. A compound of claim 1 wherein $R^2$ is hydrogen.
5. A compound of claim 1 wherein $R^2$ is lower alkyl or alkoxy.
6. The compound of claim 2, methyl 2-[4- [4-(2,4-dioxo-1-thia-3-azaspiro[4.4]nonane-3-yl)butyl]-1-piperazinylpyridine-3-cayboxylate.
7. The compound of claim 3, 2-[4-[4-(2,4-dioxo-1-thia-3-azaspiro[4.4]nonane-3-yl)butyl]1-piperazinyl]pyridine-3-carboxylate.
8. The method for ameliorating an undesirable psychotic state in a mammal comprising administration to said mammal of an effective antipsychotic amount of a compound claimed in claim 1.
9. A pharmaceutical composition in dosage unit form suitable for systemic administration to a mammalian host comprising a pharmaceutical carrier and from about 1–500 mg of a compound claimed in claim 1.

* * * * *